United States Patent
de Laat et al.

(10) Patent No.: US 10,945,439 B2
(45) Date of Patent: Mar. 16, 2021

(54) PSEUDOMONAS STRAINS AND CONSORTIA THEREOF FOR USE IN PROTECTION AGAINST PLANT DISEASES

(71) Applicant: Wim de Laat Consultancy B.V., Breda (NL)

(72) Inventors: Wilhelmus Theodorus Antonius Maria de Laat, Breda (NL); Erwin Suir, Delft (NL); Ap de Haan, Breda (NL); Joyce Josephine Elisabeth Arnouts, Achtmaal (NL)

(73) Assignee: Wim de Laat Consultancy B.V., Breda (NL)

( * ) Notice: Subject to any disclaimer, the term of this patent is extended or adjusted under 35 U.S.C. 154(b) by 110 days.

(21) Appl. No.: 16/092,457

(22) PCT Filed: Apr. 12, 2017

(86) PCT No.: PCT/EP2017/058780
§ 371 (c)(1),
(2) Date: Oct. 10, 2018

(87) PCT Pub. No.: WO2017/178529
PCT Pub. Date: Oct. 19, 2017

(65) Prior Publication Data
US 2019/0116800 A1    Apr. 25, 2019

(30) Foreign Application Priority Data

Apr. 12, 2016 (NL) ..................... 2016589
Jul. 15, 2016 (NL) ..................... 2017176

(51) Int. Cl.
| | | |
|---|---|---|
| A01N 63/00 | (2020.01) | |
| C12R 1/38 | (2006.01) | |
| C12N 1/20 | (2006.01) | |

(52) U.S. Cl.
CPC .............. *A01N 63/00* (2013.01); *C12N 1/20* (2013.01); *C12R 1/38* (2013.01)

(58) Field of Classification Search
CPC combination set(s) only.
See application file for complete search history.

(56) References Cited

FOREIGN PATENT DOCUMENTS

| EP | 1241247 A1 * | 9/2002 | .............. C12R 1/38 |
|---|---|---|---|
| EP | 1241247 A1 | 9/2002 | |
| WO | WO2014/170894 A1 | 10/2014 | |

OTHER PUBLICATIONS

El-Sayed, W. et al., Res. J. Agri. Biol. Sci 2008, vol. 4, pp. 892-901.*
Jousset, A. et al., Ecology 2014, vol. 95, pp. 1184-1190.*
Hammer, P. et al., Appl Environ Microbiol 1997 vol. 63, pp. 2147-2154.*
Validov, S. et al, J. Appl Microbiol. 2006, vol. 102, pp. 461-471.*
Alexandre Jousset et al: Biodiversity and species identity shape the anti-fungal activity of bacterial communities, Ecology, vol. 95, No. 5, May 1, 2014.
M. De Boer et al: "Control of Fusarium Wilt of Radish by Combining Pseudomonas putida Strains that have Different Disease-Suppressive Mechanisms", Phytopathology, May 1, 2003.
Saman Abeysinghe: Efficacy of combined use of biocontrol agents on control of Sclerotium rolfsii and Rhizoctonia solani of Capsicum annuum, Archiv Fuer PhytgpathOlogie und Pflanzenschutz, vol. 42, No. 3, Mar. 1, 2009 pp. 221-227.
R. Fukui et al: Interaction between strains of pseudomonads in sugar beet spermospheres and their relationship to pericarp colonization by Pythium ultimum in soil, Phytopathology, vol. 84, No. 11, Nov. 1, 1994, pp. 1322-1330.
Natalia Malfanova et al: Is-arabinose important for the endophytic lifestyle of spp.?, Archives of Microbiology, Springer. Berlin, DE, vol. 195, No. 1, Sep. 7, 2012 (Sep. 7, 2012), pp. 9-17.
Mrabet Moncef et al: Efficacy of selected Pseudomonas strains for biocontrol of Rhizoctonia solani in potato, Phytopathologia Mediterranea, Edizioni Agricole, Bologna, IT, vol. 52, No. 3, Jan. 1, 2013 (Jan. 1, 2013), pp. 449-456.
Validov S et al: Selection of bacteria able to control *Fusarium oxysporum* f. sp *radicis-lycopersici* in stonewool substrate Journal of Applied Microbiology, Wiley-Blackwell Publishing Ltd, GB, vol. 102, No. 2, Feb. 1, 2007, pp. 461-471.
Rajkumar, M., Hyu Lee Wang, and Kui Jae Lee. "Screening of bacterial antagonists for biological control of Phytophthora blight of pepper." Journal of basic microbiology 45, No. 1 (2005): 55-63.
Haas, D. "Regulation of antibiotic production in root colonizing *Pseudomonas* spp. and relevance for biological control of plant disease." Annu. Rev. Phytopathol. 41 (2003): 117-153.
Zhou, T., et al. "Isolation and characterization of Pseudomonas brassicacearum J12 as an antagonist against Ralstonia solanacearum and identification of its antimicrobial components." Microbiological research 167.7 (2012): 388.

* cited by examiner

*Primary Examiner* — Heidi Reese
(74) *Attorney, Agent, or Firm* — N.V. Nederlandsch Octrooibureau; Catherine A. Shultz; Tamara C. Stegmann

(57) ABSTRACT

The present invention relates *Pseudomonas* strains and consortia thereof that are useful in protecting plants against microbial plant diseases caused by pathogens such as *Ralstonia*, *Clavibacter*, *Erwinia*, *Curtobacterium*, *Fusarium*, *Phytophthora* and *Helminthosporium*. The *Pseudomonas* strains were selected on the basis of their antagonistic abilities against plant pathogens such as production of antimicrobial compounds, direct inhibition of growth of plant pathogens, competition of carbon or nitrogen sources and endophytic features such as anaerobic growth on nitrate as electron acceptor and growth on arabinose as carbon source. The invention further relates to compositions comprising the strains or consortia of the invention, preferably lyophilized compositions, and to methods wherein they are used in protecting a wide variety of plants against a wide variety of microbial plant diseases.

12 Claims, 1 Drawing Sheet

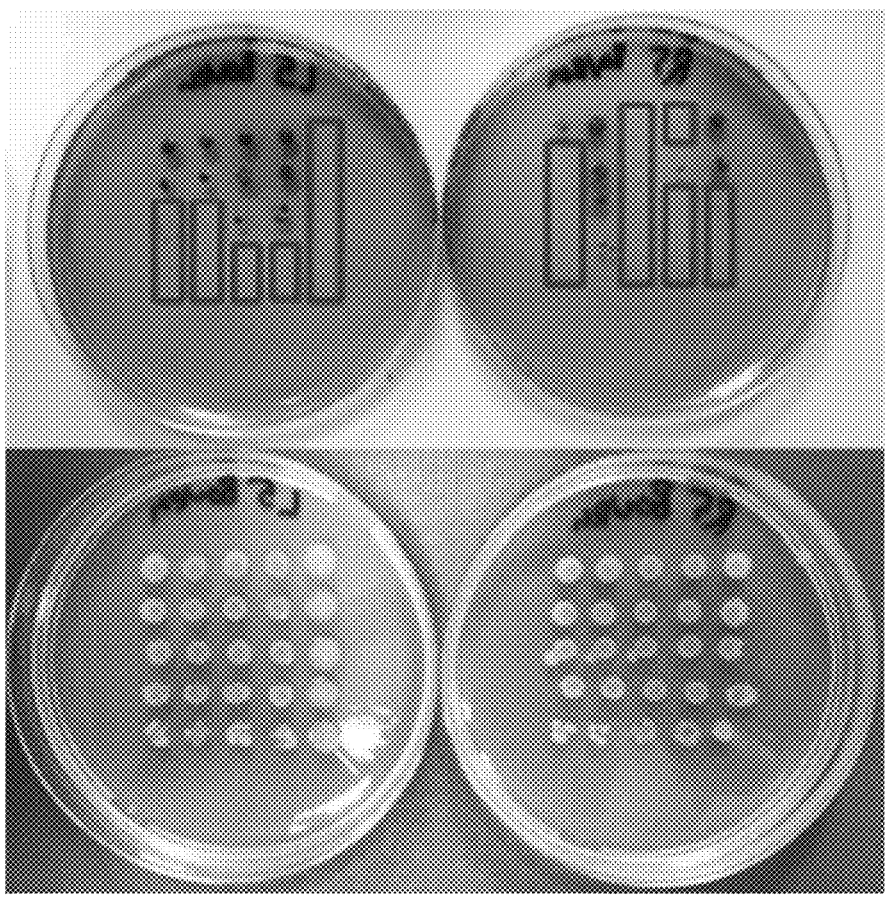

PSEUDOMONAS STRAINS AND CONSORTIA THEREOF FOR USE IN PROTECTION AGAINST PLANT DISEASES

FIELD OF THE INVENTION

The present invention relates to the fields of agriculture and microbiology. In particular the invention relates to the bacterial strains of the genus *Pseudomonas* and consortia thereof for use in protection of plants against plant diseases caused by microbial plant pathogens.

BACKGROUND OF THE INVENTION

Diseases caused by phytopathogenic bacteria, oomycetes and fungi are widespread and the cause substantial crop losses in most areas of the world. Germicides are usually used as a solution to the problems of pathogen attack; however, their use results in serious environmental problems. Moreover, for some plant pathogens there are no effective chemicals means of control so far, such as e.g. for bacterial wilt caused by *Ralstonia solanacearum*. This has spurred an increasing interest in using beneficial microorganisms as a solution to the overuse of potentially harmful pesticides. Some rhizobacteria have e.g. been used as biological agents to control plant pathogens such as *Phytophthora* (Rajkumar et al., J Basic Microbiol 2005; 45:55-63). And some strains of *Pseudomonas fluorescens* have been reported to present biocontrol properties, protecting the roots of some plant species against parasitic fungi such as *Fusarium* or *Pythium*, as well as some phytophagous nematodes, as reviewed by Haas and Keel (2003, Ann. Rev. Phytopathol. 41:117-153). Zhou et al. (Microbiol. Res. 2012; 167:388-394) reported the isolation of a *Pseudomonas brassicacearum* strain from the rhizosphere soil of tomato plants with some antagonistic activity against the plant pathogen *Ralstonia solanacearum*.

EP 1 241 247 A1 discloses mixtures of antagonistic bacteria inhibiting the growth of phytopathogenic fungi, in particular combinations of two or three different strains comprising at least *Pseudomonas chlororaphis* and *Pseudomonas putida*.

Jousset et al. (2014, Ecology, 95(5): 1184-1190) discloses in vitro tests demonstrating that a diversity of a combination of *Pseudomonas* strains (including *P. fluorescens, P. protegens* and *P. brassicacearum*) enhances the production of the antifungal compound 2,4-diacetylphloroglucinol.

Validov et al. (2007 J. of Appl. Microbiol. 102: 451-471) did grow and dry Pseudomonads using spray drying or freeze drying using skim milk and sugar. However, these authors saw a dramatic drop in CFU (colony forming units) upon freeze drying (99%) and even more during spray drying (99.5%).

There is however still a need in the art for improved means and methods for treatment and prevention of microbial plant diseases that are widely applicable at the level of seed producers, plant cutting producers as well as vegetable, crop and flower growers. It is an object of the present invention to provide for such means and methods.

DESCRIPTION OF THE INVENTION

In a first aspect the invention pertains to a consortium of different bacterial strains that act as antagonists of microbial plant pathogens. A consortium of different antagonistic strains is more effective in competing with the pathogens than an individual strain alone because the consortium can be assembled on the basis of different agonistic properties that are less likely to be found in a single bacterial strain. Such agonistic properties preferably include one or more of 1) the ability to compete for carbon sources (trophic networks); 2) the ability to compete for nitrogen sources; 3) the ability to use nitrate as electron acceptor under conditions of low oxygen concentration, as may be present in niches such as wet conditions in the rhizosphere (especially under wet soil conditions), as well as low oxygen conditions that occur in the xyleme; 4) the ability to produce a wide spectrum of antibiotic compounds to inhibit the growth of the target pathogens, and optionally resistance to the antibiotic compounds produced by other strains in the consortium; and, 5) the ability to antagonize the pathogen in more than one, preferably all, relevant zones of the target plant, including the root zone, endophytically (in the plant) as well as on the phyllosphere (on the leaf). Preferably therefore, the consortium of the invention includes one or more of 1) strains that are able to grow as an endophyt; 2) strains that are able to colonize rhizosphere; and 3) strains that are able to colonize the phyllosphere and survive in the harsh conditions thereof, e.g. by being UV- and drought-resistant.

In addition to these antagonistic abilities, the strains in the consortium preferably also have properties that facilitated their production and practical application. Preferably therefore, the strains in the consortium can be grown in industrial fermentation media to high cell densities, e.g. $10^9$/ml preferably higher than $10^{10}$/ml, even more preferably $>10^{11}$/ml and most preferably $>10^{12}$/ml. And, preferably the strains in the consortium have the ability to be produced in stabilized form allowing them to be packaged and stored before use. Preferably, therefore the strains in the consortium can be produced as a lyophilized formulation at high viable cell count.

A consortium of bacterial strains is herein understood as a combination of at least two different bacterial strains that are applied and act together in the prevention and/or treatment of plant diseases caused by microbial plant pathogens. The (at least two) different bacterial strains in the consortium can be present in a single composition. However, the (at least two) different bacterial strains in the consortium can be present in on more than one different compositions, e.g. each composition comprising at least one of the strains in the consortium. In such instances, the consortium can be a kit of parts comprising at least two different compositions, each composition comprising at least one of the strains in the consortium, and whereby preferably the comprising at least two different compositions are intended to be used in combination, as may e.g. be described in a manual for use that may also be part of the kit. It is further understood that the consortium can comprise two, three, four, five, six, seven, eight, nine, ten or more different bacterial strains.

A consortium of the invention thus comprises at least two different bacterial strains, whereby preferably, the consortium comprises: a) at least one strain that inhibits growth of a microbial plant pathogen; b) at least one strain that grows anaerobically on nitrate as electron acceptor; and, c) at least one strain that grows on arabinose. It is understood that any given strain in the consortium can have more than one of the features a), b) and c).

Preferably, the strain in the consortium that inhibits growth of a microbial plant pathogen, inhibits the growth of at least one microbial plant pathogen selected from the group consisting of *Ralstonia, Clavibacter, Erwinia, Xanthomonas, Curtobacterium, Fusarium, Phytophthora Rhizoctonia, Botrytis, Pythium, Verticillium*, and *Helminthosporium*. More preferably the strain inhibits growth of at least one microbial plant pathogen selected from the group consisting of *Ralstonia solaneacerum, Clavibacter michiganensis, Clavibacter michiganensis* ssp *michiganensis, Clavibacter michiganensis,* ssp *sepedonicus, Erwinia pectovorans, Erwinia* carotovorans, *Curtobacterium flaccumfaciens, Xanthomonas campestris, Xanthomonas fragariae, Xanthomonas campestris,* pv. Dieffenbachiae, *Xanthomonas hortorum,* pv Pelargonii, *Fusarium oxysporum, Phytophthora infestans, Phytophthora cactorum, Rhizoctonia* phalaenopsis, Botryotinia fuckeliana, *Pythium* spp., *Pythium ultimum, Verticillium dahliae, V. albo-atrum, V. longisporum,* V. nubilum, V. theobromae and V. tricorpus and *Helminthosporium solani*. The ability of a strain or a consortium of strains to inhibit growth of a microbial plant pathogen is preferably assayed as described in the Examples herein. This can e.g. be done by co-cultivation of the strain or the consortium with the pathogen and plating dilutions of samples taken at given time intervals on plates selective for the pathogen.

Preferably, the bacterial strains in the consortium are strains of the genus *Pseudomonas*. Pseudomonads are generally present in the rhizosphere, endophytic as well as on the phyllosphere (2007, Microbial ecology, 53:524-536). In addition, they are known to produce growth inhibiting compounds that inhibit the growth of *Ralstonia* (2015, Biological Control 86:14-19), *Clavibacter* (2010, World J. Microbiol. Biotechnol. 26:1059-1065), *Xanthomonas* (Walailak J. Sci & Technol. 2009; 6: 79-91), as well as antifungal compounds that are active against Phythium, *Fusarium* and *Phytophthora*. Different antimicrobial compounds have been reported to be produced by Pseudomonads such as 2,4-diacetylphloroglucinol (2,4-DAPG), HCN, Pyrrrolnitrin, pyoluteorin (PRN), Phenazine-1-carboxylate (PCA), Pyoluteorin (Plt), Cyclic Lipopeptides (CLP).

Preferably, therefore, the at least two different bacterial strains in a consortium of the invention are strains the genus *Pseudomonas*. However, preferably the consortium does not comprise strains of *Pseudomonas* species that are potentially harmful to or that are pathogens of one or more of humans, animals or plants, such as *Pseudomonas* aeroginosa, which can grow at 41° C., or *Pseudomonas syringae*. Preferably therefore none of the strains in the consortium belongs to a species selected from *Pseudomonas syringae* and *Pseudomonas aeruginosa*.

In one embodiment, the consortium also does not comprise a *Pseudomonas fluorescens* strain. In another embodiment, the consortium also does not comprise at least one of a *Pseudomonas fluorescens* or a *Pseudomonas chlororaphis* strain.

In one embodiment, at least one strain in the consortium produces or has the ability to produce an antimicrobial compound that inhibits the growth of a microbial plant pathogen. Preferably, the antimicrobial compound is selected from the group consisting of HCN, 2,4-diacetylphloroglucinol, phenazines, pyrrolnitrin, pyoluteorin and cyclic lipopeptides. The ability to produce an antimicrobial compound that inhibits the growth of a microbial plant pathogen can be tested as described in the Examples herein, e.g. by detecting halo's around the strain producing the compound in a field of the plant pathogen plated on agar. Alternatively, the ability of a strain in the consortium can be tested by determining the presence of genes involved in the production of the antimicrobial compound. Such *Pseudomonas* genes and PCR primers for their detection are described in Kim et al. (2013, J. Agric. Chem. Environ. Vol 2, No 1. pp 8-15). Preferably, therefore, at least one strain in the consortium comprises genes for the production of an antimicrobial compound selected from the group consisting of HCN, 2,4-diacetylphloroglucinol, phenazines, pyrrolnitrin, pyoluteorin and cyclic lipopeptides. Preferably the consortium is composed such that together the strains in the consortium comprise as many of these genes for the production of an antimicrobial compound. The consortium thus preferably comprises one or more strains which together comprise at least 2, 3, 4, 5 or all 6 of the genes for the production of an antimicrobial compound selected from the group consisting of HCN, 2,4-diacetylphloroglucinol, phenazines, pyrrolnitrin, pyoluteorin and cyclic lipopeptides.

In another embodiment, at least one strain in the consortium is a strain that grows on nitrate as electron acceptor, preferably under anaerobic conditions. "Anaerobic or anoxic conditions" are herein defined as conditions substantially in the absence of oxygen and wherein molecules other than oxygen serve as electron acceptors. Under anoxic conditions substantially no oxygen is consumed, preferably less than 5, 2, 1, or 0.5 mmol/L/h, more preferably 0 mmol/L/h is consumed (i.e. oxygen consumption is not detectable), or substantially no dissolved oxygen can be detected in the growth medium, preferably the dissolved oxygen concentration in the medium is less than 2, 1, 0.5, 0.2, 0.1% of air saturation, i.e. below the detection limit of commercial oxygen probes. Strains that grow on nitrate as electron acceptor, preferably under anaerobic conditions, can be strains that belong to a species selected from *P. protegens, P. brassicacearum,* and *P. putida,* such as e.g. the strains Pr, Br, 86, 80, 27 and 20.

In another embodiment, at least one strain in the consortium is a strain that grows on arabinose as carbon and/or energy source. Preferably, the strain grows on arabinose as sole carbon and/or energy source. Strains that grow on arabinose as (sole) carbon and/or energy source can be strains that belong to a species selected from *P. moraviensis, P. reinekei,* and *P. putida, P. brassicacearum* such as e.g. the strains Br, 20, 55, 80, 17, 11, 29 and 86.

In a preferred embodiment, the consortium comprises at least one strain that is an endophytic strain. The endophytic strain preferably is a strain that grows on arabinose as carbon and/or energy source, preferably as sole carbon and/or energy source, and/or that grows on nitrate as electron acceptor, preferably under anaerobic conditions. Preferred endophytic strains of the invention include e.g. the strains Br, 20, 27, 80 and 86. More preferred endophytic strains of the invention include e.g. the strains Pr, Br, 20, 27, 80, 29, 11 and 86.

A preferred consortium according to the invention is a consortium wherein at least one of: a) the *Pseudomonas* strain that inhibits growth of a microbial plant pathogen belongs to a species selected from *P. moraviensis, P. protegens, P. brassicacearum* and *P. putida;* b) the *Pseudomonas* strain that grows anaerobically on nitrate as electron acceptor belongs to a species selected from *P. protegens, P. brassicacearum, P. reinekei,* and *P. putida;* and, c) wherein a *Pseudomonas* strain that grows on arabinose belongs to a species selected from *P. moraviensis, P. reinekei,* and *P. putida.*

A further preferred consortium according to the invention is a consortium wherein at least one of: a) the *Pseudomonas* strain that inhibits growth of a microbial plant pathogen belongs to a species selected from *P. moraviensis, P. protegens, P. brassicacearum, P. palleroniana,* and *P. putida, P. extremaustralis;* b) the *Pseudomonas* strain that grows anaerobically on nitrate as electron acceptor belongs to a species selected from *P. protegens, P. brassicacearum, P. reinekei*, and *P. putida*; and, c) wherein a *Pseudomonas* strain that grows on arabinose belongs to a species selected from *P. moraviensis, P. brassicacearum, P. reinekei*, and *P. putida, P. extremaustralis*.

Preferably, a consortium of the invention is composed to comprise at least 2, 3, 4, 5, 6, 7, 8, 9 or 10 different *Pseudomonas* strains, wherein the consortium comprises: a) one or more strains as defined above which together comprise at least 2, 3, 4, 5 or all 6 of the genes for the production of an antimicrobial compound selected from the group consisting of HCN, 2,4-diacetylphloroglucinol, phenazines, pyrrolnitrin, pyoluteorin and cyclic lipopeptides; b) a strain as defined above that grows on nitrate as electron acceptor, preferably under anaerobic conditions; and c) a strain as defined above that grows on arabinose as carbon and/or energy source.

An example of such a preferred consortium is a consortium comprising at least 2, 3 or 4 strains selected from the strains 17, 55, Pr, Br and 27. More preferably the consortium comprises at least 2 or 3 strains 17, 55, Pr and Br. Even more preferably is a consortium of at least 5, 6, 7 or 8 strains selected from the strains 24, Pr, Br, 17, 27, 20, 55 and 80. A particularly preferred consortium has a broad antibiotic production profile in addition to the abilities to grow on arabinose and to reduce nitrate, such as e.g. a consortium comprising at least the strains 24, Pr, Br, 17, 27, 20, 55 and 80 or a consortium comprising at least the strains 24, Pr, Br, 17, 27, 20, 55, 11, 29 and 80. These preferred consortia are useful for the prevention and/or treatment of bacterial plant diseases, preferably plant diseases caused by bacteria selected from *Ralstonia, Clavibacter, Erwinia, Xanthomonas* and *Curtobacterium*, more preferably, plant diseases caused by *Ralstonia*, e.g. *Ralstonia* solaneacerum.

A preferred consortium for use against plant pathogenic fungi at least includes a strain of the species *Pseudomonas palleroniana, P. protegens, P. brassicacearum* and *P. putida*, more preferably, the consortium includes one or more strains selected from the strains 24, 27, 80, Pr and Br. These preferred consortia are useful for the prevention and/or treatment of fungal plant diseases, preferably plant diseases caused by fungal selected from *Fusarium, Phytophthora, Rhizoctonia, Botrytis, Pythium, Verticillium*, and *Helminthosporium*. Consortia for use against *Phytophthora* preferably at least include a strain of the species *Pseudomonas palleroniana, P. moraviensis* and *P. brassicacearum* more preferably strain 24, 11 and Br. Consortia for use against *Fusarium* preferably at least include a strain of the species *P. protegens, P. brassicacearum* and *P. putida*, more preferably one or more of strains 27, 80, Pr and Br.

A further preferred consortium is useful against both plant pathogenic fungi and bacteria and comprises at least one or more strains selected from the strains 24, 27, 80, Pr and Br, and at least 2, 3 or 4 strains selected from the strains 17, 55, Pr, Br and 27.

In a further aspect, the invention relates to compositions comprising a strain or a consortium according of the invention. Thus, the invention relates to a consortium as herein defined, wherein the strain or consortium is comprised in one or more compositions, each composition comprising one or more of the strains of the consortium and an agriculturally acceptable carrier. The agriculturally acceptable carrier preferably is an inert material that facilitates that storage and application of the strains or the strains in the consortium. The carrier can be for a liquid or solid formulation of the strains. By inert carriers, we mean any material that preferably does not biologically react with the bacteria and plants. Examples of inert carrier materials include e.g. talc, silica, fir bark, perlite, vermiculite, alginate, and clay. In a preferred embodiment, a composition comprising the strains of the consortium is a lyophilized or air dried (e.g. fluid bed dried or spray-dried) composition. The lyophilized or air dried composition may include one or more (cryo) protective compounds including e.g. polyols such as ethyleneglycol, 1,3, propanediol, glycerol, erythritol, sorbitol, mannitol, arabitol or xylitol or sugars such as sucrose and trehalose. And support compounds such as skim milk and maltodextrines, starch etc.

Preferably a strain, or each strain of the consortium is present (in the one or more compositions) at a concentration ranging from about $1 \times 10^2$, $10^3$, $10^4$, $10^5$, or $10^6$ to about $1 \times 10^7$, $10^8$, $10^9$, $10^{10}$, or $10^{11}$ CFU per gram. More preferably, a strain, or each strain of the consortium, is present at a concentration that is higher than about $1 \times 10^8$, $10^9$, $10^{10}$, or $10^{11}$ CFU per gram.

In a further aspect, the invention relates to a method for protecting plants against a plant pathogen comprising applying to plants, plant tubers, plant seeds, plant roots or soil surrounding plants, plant tubers, plant seeds, plant roots or plant cuttings, a strain or a consortium as defined herein, under conditions effective to protect said plants or the plants produced from said plant cuttings, tubers or seeds against the plant pathogen. Preferably, the method is a method for preventing and/or treating a plant disease caused by a plant pathogen is a selected from the group consisting of *Ralstonia, Clavibacter, Erwinia, Xanthomonas, Curtobacterium, Fusarium, Phytophthora, Verticillium, Botrytis, Pythium, Rhizoctonia* and *Helminthosporium*. In one embodiment of the method, the strain or consortium is used to treat the plant by topical application or to treat soil around the plant's roots. In another embodiment of the invention, the strain or consortium is applied to seed of the plant. The strain or consortium can applied by coating onto the seed, immersion of the seed into and/or by spraying of the seed with liquid comprising the (resuspended) strain or consortium or by supplying the strain or consortium to the roots, preferably resuspended in a liquid and e.g. by dosing via an irrigation system with different intervals such as once per week or once per two weeks. The strain or consortium may also be maintained after the initial administration/application by adding nutrients that are selected for specifically enhancing the growth of Pseudomonads.

The consortia or strains of the invention can be employed in the methods of the invention for protecting, preventing or treating disease in any plant species, including, but not limited to, monocots and dicots. Examples of plant species of interest include, but are not limited to, corn (*Zea mays*), *Brassica* sp. (e.g., *B. napus, B. rapa, B. juncea*), alfalfa (*Medicago sativa*), rice (*Oryza sativa*), rye (*Secale* cerecile), sorghum (*Sorghum bicolor, Sorghum vulgare*), millet (e.g. pearl millet (*Pennisetum glaucum*), proso millet (*Panicum mitiaceum*), foxtail millet (*Setaria italica*), finger millet (*Eleusine* corcicana)), sunflower (*Helianthus annuus*), safflower (Carthamus tinctorius), wheat (*Triticum aestivum*), soybean (*Glycine max*), tobacco (*Nicotiana tabacum*), potato (*Solanum tuberosum*), peanuts (*Arachis hypogaea*), cotton (*Gossypium* barbaclense, *Gossypium hirsutum*), sweet potato (*Ipomoea batatus*), cassava (*Manihot esculenta*), coffee (*Cojfea* spp.), coconut (*Cocos* nucifera), pineapple (*Ananas comosus*), citrus trees (Citrus spp.), cocoa (*Theobroma cacao*), tea (*Camellia sinensis*), banana (Musa spp.), avocado (*Persea americana*), fig (*Ficus* ccisica), guava (*Psidium guajava*), mango (*Mangifera indica*), olive (*Olea europaea*), papaya (*Carica papaya*), cashew (Ancicardium *occidentale*), macadamia (Macadamia integrifolia), almond (*Prunus* amygdalus), sugar beets (*Beta vulgaris*), sugarcane (*Saccharum* spp.), oats, barley, vegetables, omamentals, and conifers. Vegetables include tomatoes (*Solanum lycopersicum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (C. cantalupensis) and musk melon (*C. melo*). Ornamentals include e.g. azalea (*Rhododendron* spp.), hydrangea (*Macrophylla hydrangea*), hibiscus (Hibiscus rosasanensis), roses (Rosa spp.), tulips (Tulipci spp.), daffodils (*Narcissus* spp.), petunias (*Petunia hybrida*), carnation (*Dianthus* ccuyophyllus), poinsettia (*Euphorbia pulcherrima*), Gerbera, Anthurium, Salvia, Heuchera, Heucherella, Tiarella, *Begonia* and Coreopsis and *Chrysanthemum*. Conifers that may be employed in practicing the present invention include e.g. pines such as loblolly pine (*Pinus taeda*), slash pine (*Pinus* elliotii), *ponderosa* pine (*Pinus ponderosa*), lodgepole pine (*Pinus contorta*), and Monterey pine (*Pinus radiata*), Douglas-fir (*Pseudotsuga menziesii*), Western hemlock (*Tsuga canadensis*), Sitka spruce (*Picea glauca*), redwood (*Sequoia sempervirens*), true firs such as silver fir (*Abies amabilis*) and balsam fir (*Abies balsamea*), and cedars such as Western red cedar (Thujaplicata) and Alaska yellow-cedar (*Chamaecyparis nootkatensis*). In specific embodiments, plants of the present invention are crop plants including for example, corn, alfalfa, sunflower, *Brassica*, soybean, cotton, safflower, peanut, *sorghum*, wheat, millet, tobacco, apple, pear, strawberry, grapes (for wine), Eggplant (*Solanum melongena*), bell pepper and other peppers, onions, carrot (*Daucus carota* subsp. *sativus*), etc.

In a further aspect, the invention relates to a method of growing a plant. Preferably in the method of growing a plant, the plant is protected against plant pathogens. The methods comprises a) growing the plant and b) applying to the plant, or to plant cuttings, tubers, seeds from which the plant is grown, or to soil surrounding the plant's roots, a strain or a consortium of strains as herein defined, under conditions effective to protect said plants or the plants against said plant pathogens, and optionally comprising the step of harvesting the plant or a produce from said plant. Preferably, in the method, the plant and the plant and the pathogen are as herein defined above. In one embodiment, of the method, the consortium is used to treat the plant by topical application or to treat soil around the plant's roots. In another embodiment of the invention, the strain or consortium is applied to seed of the plant. The strain or consortium can applied by coating onto the seed, immersion of the seed into and/or by spraying of the seed with liquid comprising the (resuspended) strain or consortium or by supplying the strain or consortium to the roots, preferably resuspended in a liquid and e.g. by dosing via an irrigation system with different intervals such as once per week or once per two weeks. The strain or consortium populations may also be maintained after the initial administration/application by adding nutrients that are selected for specifically enhancing the growth of Pseudomonads.

In yet a further aspect, the invention pertains to the use of a strain or a consortium as herein defined, for protecting a plant as herein defined against a plant pathogen as herein defined, preferably using the methods as herein defined.

In yet a further aspect, the invention pertains to the specific strains with beneficial properties as defined herein, which strains were identified by the present inventors and deposited on 8 Apr. 2016 at the Centraalbureau voor Schimmelcultures (Utrecht, The Netherlands), under the regulations of the Budapest Treaty. These strains include: *Pseudomonas moraviensis* strain 17, having Accession No. CBS 141219; *Pseudomonas putida* #20, having Accession No. CBS 141220; *Pseudomonas palleroniana* #24, having Accession No. CBS 141221; *Pseudomonas putida* #27, having Accession No. CBS 141222; *Pseudomonas reinekei* #55, having Accession No. CBS 141223; *Pseudomonas putida* #80, having Accession No. CBS 141224; *Pseudomonas putida* #86, having Accession No. CBS 141225; *Pseudomonas brassicacearum* BRO1, having Accession No. CBS 141226; *Pseudomonas protegens* PR01, having Accession No. CBS 141227; *Pseudomonas moraviensis* #11, having accession No. CBS 141646; *Pseudomonas* sp. #29, having accession No. CBS 141647. The latter two strains were deposited on 12 Jul. 2016 at the Centraalbureau voor Schimmelcultures (Utrecht, The Netherlands), under the regulations of the Budapest Treaty.

In another aspect, the invention pertains to a method for producing a composition comprising a strain or a consortium according to the invention. The method preferably comprising the steps of: a) growing a bacterial strain as defined herein to a density that is higher than about $1 \times 10^8$, $10^9$, $10^{10}$, or $5 \times 10^{11}$ CFU/ml; b) optionally, at least one of concentrating and drying cells of the strain obtained in a); and, c) formulating the composition comprising a strain or a consortium of strain and an agriculturally acceptable carrier. The drying of the strain can be achieved by any drying method available to the skilled person, such as spray-drying, freeze drying, vacuum drying, belt drying, fluid bed drying and microwave drying. It is also understood that a one or more consortium of the strains can be mixed together prior to the concentration and/or drying steps. Alternatively, the strains are concentrated and/or dried separately. In a preferred embodiment, the method for producing a composition comprising a strain or a consortium according to the invention obviates the need of concentrating the cells of the strain obtained in a). Such a preferred method thus comprises the steps of: a) growing a bacterial strain as defined herein to a density that is higher than about $1 \times 10^8$, $10^9$, $10^{10}$, or $5 \times 10^{11}$ CFU/ml; b) drying cells of the strain obtained in a); and, optionally, c) formulating the composition comprising a strain or a consortium of strains and an agriculturally acceptable carrier.

In a yet another aspect, the invention relates to a method for drying a composition comprising viable bacteria, preferably Gram-negative bacteria. Preferably, in the method a dry composition of viable bacteria is produced that retains a high viable cell count. Drying of Gram negative microbes such as Pseudomonads while retaining high viable cell count has been very difficult so far. In this invention we provide means and methods to produce high viable cell counts both in freeze drying and spray drying. In particular, spray-drying Gram negative bacteria at high survival rates so far has never been reported.

The drying process can include one or more of spray-drying, freeze drying, vacuum drying, belt drying, fluid bed drying and microwave drying. A preferred method of drying is or involves a form of air drying such as e.g. spray-drying or fluid-bed drying. Especially when sustainable agriculture grows to maturity the bacteria to be applied therein need to be produced at large scale, at which (hot) air-based drying techniques, such as spray drying and fluid bed drying, are advantageous over freeze drying.

In one embodiment therefore, the invention relates to a method for producing a solid composition comprising viable bacteria. The composition preferably is a dry solid composition. The method preferably comprises the steps of: a)

preparing a suspension of the bacteria in an aqueous solution comprising a polyol having structure (I); and, b) drying the suspension prepared in step (a) by removal of water so as to obtain the solid composition comprising viable bacteria. The polyol preferably has the structure (I): $R^1R^2R^3C-CR^4R^5R^6$, wherein $R^1$=H, OH or $CR^7R^8OH$, each of $R^2$-$R^8$ is individually selected from H and OH, wherein at least 1 of $R^2$-$R^8$ is OH or in case $R^1$=H at least 2 of $R^2$-$R^6$ are OH, and if $R^1$=$CH_2OH$ at least one of $R^4$-$R^6$ is OH. Preferably the polyol having structure (I) is selected from glycerol, ethyleneglycol and 1,3-propandiol. The suspension prepared in step (a) preferably comprises at least 0.1, 0.2, 0.3, 0.4, 0.5, 0.6, 0.7, 0.8, 0.9, 1.0, 1.1, 1.2, 1.25, 1.3, 1.4, 1.5, 2.0, 2.5, 3.0 or 4% (w/w) of the polyol having structure (I), depending on the amount of bacteria (as dry matter) in the suspension. More preferably therefore, the amount glycerol in the suspension in step (a) is chosen so as to obtain a weight percentage of the polyol having structure (I) on dry matter in the range of 0.1 and 20% in the solid composition comprising viable bacteria. Preferably, the weight percentage of the polyol having structure (I)on dry matter in the solid composition comprising viable bacteria is at least 0.1, 0.2, 0.5, 1.0, 2.0, 3.0, 4.0, 5.0, 6.0 or 7.0% (w/w) and no more than 20, 15, 12, 11, 10, 9.0, or 8.0% (w/w). In a preferred embodiment, the suspension of the bacteria in an aqueous solution comprising the polyol is prepared by mixing the polyol directly with a high density culture of the bacteria. This obviates the need for an additional concentration step. A high density culture is defined herein as a density of that is higher than about $1 \times 10^8$, $10^9$, $10^{10}$, or $5 \times 10^{11}$ CFU/ml.

In a preferred method, the drying in step (b) includes one or more of spray-drying, freeze drying, vacuum drying, belt drying, fluid bed drying and microwave drying, more preferably, the drying is or involves a form of air drying such as e.g. spray-drying or fluid-bed drying. Fluid bed drying can be done at bed temperature of about 25, 30, 35, 40, or 45° C., preferably about 28-32° C., such as about 30° C. Outlet temperature during spray drying can be about 35, 40, 45, 50, 55, 60, 65, 70, 75 or 80° C., preferably about 35-55, most preferably in the range of about 40-50° C.

It is further preferred in the method that in step (b), the solution of step (a) is dried by the removal of water so as to obtain a dry (solid) composition comprising viable bacteria with a dry matter content of at least 80, 85, 88, 90, 91, 92, 93, 94, 95, 96, 97, 98 or 99% (w/w).

The inventors have surprisingly discovered that the application of a polyol having structure (I), such as e.g. glycerol, ethyleneglycol or 1,3-propandiol is important for obtaining a good bacterial survival rate during spray drying. In a preferred method therefore, the viable cell count of the bacteria in the dry (solid) composition obtained in step (b) is at least 50, 55, 60, 65, 70, 73, 75, 80, 85 or 90% of the viable cell count of the bacteria in the solution of step (a).

In addition to the polyol having structure (I) or a mixture of such polyols, the aqueous solution comprising the bacteria to be dried can further comprise at least one of erythritol, sorbitol, mannitol, xylitol, sugars (such as sucrose and trehalose), and optionally support materials such as skim milk, maltodextrines and/or starch. Preferably, the aqueous solution comprises at least one of: a) at least 0.1, 0.2, 0.5, 1.0, 2, 4, 6, 8, 10, 12 or 15% (w/w) sugar; and, b) at least 0.1, 0.2, 0.5, 1.0, 2%, 5%, 10%, 20%, 40% or 50% (w/w) skim milk.

Preferably, the method for producing a dry (solid) composition comprising viable bacteria is a method wherein the composition comprises a Gram-negative bacterium. More preferably, the Gram-negative bacterium is a Pseudomonad. Preferably, the Pseudomonad is of a species selected from *P. moraviensis, P. protegens, P. brassicacearum, P. putida, P. reinekei, P. fluorescens* and *P. palleroniana*.

In order to realize high recovery rates of Pseudomonads we discovered that application of glycerol is crucial not only to reach good freezing results, but especially to get good survival during spray drying. A preferred mix of Cryoprotectants was discovered to be a mix of Skim milk, sucrose and a polyol having structure (I), of which preferably glycerol, ethyleneglycol and/or 1,3-propanediol.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

All patent and literature references cited in the present specification are hereby incorporated by reference in their entirety.

The following examples are offered for illustrative purposes only, and are not intended to limit the scope of the present invention in any way.

DESCRIPTION OF THE FIGURE

FIGURE.
Plating of co-cultures of 10 *Pseudomonas* consortia with *Ralstonia* (mix of two strains, one strain (LMG2291 being race 3, biovar 2 and one strain RS03 being race 1) as described in the Examples. After 4 days of co-culture 4 ul per incubation was spotted to a cetrimide plate (*Pseudomonas* selective, the two plates on top) and a violet plate (the two plates at the bottom) selective for *Ralstonia* (SMSA+ TTC). The plates were incubated for 2 days at 28° C. before they were photographed. The left-hand plates present from left to right, respectively, the consortia A to E, the right-hand plates present from left to right, respectively, the consortia F to E. The columns on the plates are from top to bottom, respectively, dilutions of $10^{-1}$, $10^{-2}$, $10^{-3}$, $10^{-4}$ and $10^{-5}$.

Examples

1. Selection of *Pseudomonas* Strains for Use in Protection Against Plant Diseases We obtained some 90 microbial strains from various sources of which we assumed they would belong to the group of (fluorescent) Pseudomonads as the strains were isolated on *Pseudomonas*-selective cetrimide plates (Tritium microbiology, Eindhoven) to demonstrate the ability to produce fluorescent compounds at room temperature (21° C.) or at 4° C.

The strains were screened using a set of fluorescent Pseudomonad-specific PCR primers as described by Kim et al. (2013, J. Agric. Chem. Environ. Vol 2, No 1. pp 8-15). Strains positively identified as Pseudomonads were further subjected to 16S ribosomal gene-sequencing in order to identify the isolates at species level. Strains identified as *P. aeruginosa* were eliminated as potential human pathogens.

The remaining *Pseudomonas* strains were subjected to screening for their ability to use carbon and nitrogen sources as required for their ability to for compete on substrate level with the plant pathogen *Ralstonia* solaneacearum as published by Wang et al. (2015, Plant pathol. J. 14:38-34).). The strains were grown on OSG medium with the individual carbon and nitrogen sources as described for the synthetic tomato exudates as described by Wei et al (Nature communications DOI:10.1038/ncomms9413).

Next, the ability to use inorganic nitrogen sources was tested. Specifically inorganic nitrogen sources often used as fertilizer, such as nitrate, nitrite, ammonia and urea were tested for competitive utilization of these sources.

After this, the ability to grow well under anaerobic conditions in the presence of nitrate as electron acceptor was tested for the top 20 candidate strains that remained after the carbon and nitrogen utilization pattern preselection. 7 out of the 20 strains demonstrated good anaerobic growth using nitrate as electron acceptor. The competition in low oxygen condition is important as it is e.g. known that *Ralstonia* is able to utilize nitrate as electron acceptor under anaerobic or low oxygen conditions such as root zones and xyleme (Dalsing et al. (2015) mBIO 6(2):e02471-14. Doi:10.1128/mBio.02471-14). The genetic potential of the strains to produce antimicrobial compounds was tested using PCR based screening for the presence of genes necessary for the production of HCN (hcnBC genes), 2-4 DAPG (phlD gene), phenazines (phzCD genes) and pyrrolnitrin (prnD gene) and pyoluterorin (PltC). PCR primers used for detecting these genes were as described by Kim et al. (2013, supra). The presence of genes necessary for the production of lipopeptides (CLP genes) was tested using a set of primers (218_clpS/clpA_FW and 219 clpS/clpA_RV) based on a piece of DNA occurring frequently in CLP producing pseudomonads as described by Song et al. (2015, BMC Microbiology 15:29).

The antimicrobial activity of the strains was further tested on agar plates detection of halo's in a field of a plant pathogen, around the inoculated *Pseudomonas* strains. Target plant pathogenic organisms in the screening were: *Ralstonia* solaneacerum, *Erwinia carotovora* ssp *carotovora*, *Curtobacterium flaccumfaciens* and *Clavibacter michiganensis* ssp *michiganensis*, *Xanthomonas hortorum* pv. Pelargonii, *Fusarium oxysporum* and *Phytophthora infestans Botrytis cinerea, Pythium ultimum, Verticillium dahlia, Rhizoctonia solani*.

Based on this information a set of 12 strains was selected that demonstrated growth inhibition towards at least one of the target organisms. These 10 strains were further tested able to utilize arabinose, a property strongly correlated with endophytic lifestyle of Pseudomonads (Arch. Microbiol. (2013) 195:9-17 and Appl. Soil Ecol. 42:141-149).

Table 1 present an over view of these strains and their various relevant properties. The most relevant strains were deposited on 8 Apr. 2016 (#11 and #29 were deposited on Jul. 12, 2016) at the Centraalbureau voor Schimmelcultures (Utrecht, The Netherlands), under the regulations of the Budapest Treaty. Table 2 presents the accession no's of the deposited strains.

TABLE 1

| ID | Species | Phe | DAPG | pltC | prnD | CLP | HCN | *Ralstonia* inhibition Strain RS03: Race 1 48 0.1 TSB | | *Ralstonia* inhibition Strain LMG2291 Race 3, Biovar 2 48 0.1TSB | | RS03 24 0.1 TSB | *Curtobacterium* inhibition | |
|---|---|---|---|---|---|---|---|---|---|---|---|---|---|---|
| | | | | | | | | TSB | ATJ | TSB | ATJ | TSB | TSB | ATJ |
| 24 | *P. palleroniana* | + | – | – | – | + | – | – | – | – | – | – | – | – |
| PR | *P. protegens* | – | + | + | + | + | + | ++ | ++ | + | + | ++++ | + | + |
| BR | *P. brassicacearum* | – | + | – | – | + | + | + | + | – | – | +++ | ++ | + |
| 27 | *P. putida* | – | – | – | – | + | – | +/– | – | +/– | – | + | – | + |
| 20 | *P. putida* | – | – | + | – | + | – | – | – | – | – | ++ | – | +/– |
| 55 | *P. reinekei* | – | + | – | – | + | – | – | – | – | – | – | +/– | +/– |
| 80 | *P. putida* | – | + | – | – | + | – | + | + | + | + | +++ | +/– | +/– |
| 17 | *P. moraviensis* | – | – | + | – | + | + | +/– | – | ++ | ++ | – | – | +/– |
| 86 | *P. putida* | – | + | – | – | + | – | +/– | + | + | + | ++ | +/– | +/– |
| 11 | *P. moraviensis* | + | + | – | – | + | – | | | | | – | | |
| 29 | *Pseudomonas* sp. | – | – | – | – | + | + | | | | | ++ | | |

| ID | *Clavibacter* inhib-tion | *X. hortorum* pv *pellargoni* inhibition | *Erwinia carotocoa* ssp *carotovora* DSM30168 | Anaerobic Growth using $NO_3$ as electron acceptor | *Phytophthora* inhibition | *Fusarium* inhibitbion | Growth on arabinose |
|---|---|---|---|---|---|---|---|
| 24 | – | – | – | – | ++ | – | – |
| PR | ++++ | + | – | + | – | ++ | – |
| BR | ++++ | + | + | + | ++ | ++ | + |
| 27 | – | – | – | ++ | – | ++ | + |
| 20 | – | – | – | ++ | – | – | + |
| 55 | + | – | – | – | – | – | + |
| 80 | + | – | – | + | – | ++ | + |
| 17 | – | – | – | – | – | – | + |
| 86 | + | + | – | + | – | – | + |
| 11 | + | + | + | – | + | – | + |
| 29 | | + | + | | | | + |

ATJ: Artificial tomato exudate medium based on OSG medium containing 48 carbon sources as described in carbon and nitrogen sources as described for the synthetic tomato exudates as described by Wei et al (Nature communications DOI: 10.1038/ncomms9413)

TABLE 2

| Accession no. | Strain |
| --- | --- |
| CBS 141219 | *Pseudomonas moraviensis* # 17 |
| CBS 141220 | *Pseudomonas putida* # 20 |
| CBS 141221 | *Pseudomonas palleroniana* # 24 |
| CBS 141222 | *Pseudomonas putida* # 27 |
| CBS 141223 | *Pseudomonas reinekei* # 55 |
| CBS 141224 | *Pseudomonas putida* # 80 |
| CBS 141225 | *Pseudomonas putida* # 86 |
| CBS 141226 | *Pseudomonas brassicacearum* BR01 |
| CBS 141227 | *Pseudomonas protegens* PR01 |
| CBS 141646 | *Pseudomonas moraviensis* #11 |
| CBS 141647 | *Pseudomonas* sp. #29* |

*CBS 141647 has been determined to be *Pseudomonas extremaustralis* strain #29

2. Consortia of Strains for Biocontrol Against Various Plant Pathogens

Using the criteria of Example 1 above, a number of consortia of *Pseudomonas* strains were assembled to further enhance the inhibition of growth of the plant pathogenic bacteria and fungi. The consortia were tested for antagonistic activity against the plant pathogens *Ralstonia solanacearum* race 1 and race 3, a *Curtobacterium flaccumfaciens, Clavibacter* michigansis ssp *michiganensis* and a second *Ralstonia* solaneacearum race 1 (occurring in roses in the Netherlands).

As a laboratory screen to demonstrate elimination of *Ralstonia solanacearum* we grew two *Ralstonia* strains for 2 days on 0.1 TSB (Tryptic soy broth) medium at 28° C., one isolated from plant material; *Ralstonia* solancearum RS03 (Race 1) obtained from Dummen Group, and one *Ralstonia* solancearum LMG2291 (Race 3). The cultures were diluted and then inoculated to a chemically defined (OSG) medium at pH 5.8 using an artificial tomato juice comprising the 48 carbon sources from Wang et al. (2015, Plant pathology journal 14, 38-34) at a concentration of 0.025 gr/L each and applying 1.5 gr/L $NaNO_3$ as nitrogen source using a MOPS buffer at 10 gr/L to control pH between 6 and 7 upon cultivation to prevent too drastic pH increase upon growing on nitrate. OSG medium is described by Ornston and Stanier (1966, J. Biol. Chem. 241:3776-86).

8 Pseudomonads were grown individually on 0.1 TSB medium for 24 hrs at 28° C. and inoculated in different combinations. For co-culture of *Pseudomonas* consortia with *Ralstonia* (mix of two strains) both were inoculated initially at a level of $10^7$ cells/ml in the above described “chemically defined artificial tomato juice medium”, and incubated at 20-22° C. (room temperature). Then after each day 4 ul per incubation was spotted to a cetrimide plate (*Pseudomonas* selective) and a violet plate selective for *Ralstonia* (SMSA+TTC). The plates were incubated for 2 days at 28° C. before they were assessed. Table 3 presents the *Pseudomonas* consortia that were studied. FIG. 1 presents the data obtained after 4 days of co-cultivation. This gave the following ranking of the *Pseudomonas* consortia with respect to their agonistic activity against *Ralstonia:*

1. Consortium E
2. Consortium H
3. Consortium I
4. Consortium F
5. Consortium B
6. Consortium A
7. Consortium J
8. Consortium C
9. Consortium D
10. Consortium G The *Pseudomonas moraviensis* strain number 17 appears to be one of the better strains for suppression of the two *Ralstonia*'s tested as it was present in each of the consortia in the top 3 of the ranking. After 4 days consortia E, H and I had completely eliminated $10^7$ *Ralstonia* cells/ml to less than 10 per 4 ul, as no colony appears anymore even in the $10^{-1}$ dilutions.

Also the possibly negative effect of the various *Pseudomonas* strains towards each other was tested by inoculating each the various *Pseudomonas* strains in separate holes in an agar layer of 0,1 TSB medium solidified with agar and then spreading one of the strains as a lawn and detecting growth inhibition in the lawn around the various holes. The following inhibitions were found: strain 80 inhibits growth of strain 27 and of strain Br; strain Br inhibits growth of strain 24; and strain 86 inhibits growth of strain Br.

TABLE 3

| Consortium | Strains |
|---|---|
| A | Pr, Br, 17, 20, 27, 55, 86, 71 |
| B | Pr, 17, 55, 71 |
| C | Br, 20, 27, 86 |
| D | Pr, 71 |
| E | 55,17 |
| F | Br, 20 |
| G | 27, 86 |
| H | Pr, Br, 17, 27 |
| I | Pr, Br, 17, 27, 55 |
| J | Pr, Br, 17, 27, 55, 86 |

3. Production of Pseudomonads in Economic Amounts

The organisms were produced in a fermentation process applying a high cell density glucose limited fed batch fermentation process at 28° C., pH 6.8 on a suitable chemically defined medium (see WO1998037179 A2 and OSG medium) with a duration of 24-40 hours producing a very high cell count of $5*10^{10}$-$3*10^{12}$ CFU/ml that does not need centrifugation as a concentration step. Alternatively, strains of the invention can be fermented at lower cell count, after which the cells of the strain can be concentrated by microfiltration and or centrifugation. After a batch phase of 10-12 hours consuming the 20 gr/L glucose after inoculation, a concentrated glucose (>50% glucose) feed was started and was increased to maximum flow that allowed good aeration of the culture while maintaining glucose <1 g/L. Ammonium was kept sufficiently high to enable reproduction of the cells by adding ammonium salts to the batch medium and use concentrated ammonium (>12.5% $NH_3$) as a titrant. The inoculum was a 1.5% (vol/vol) of full grown TSB medium culture prepared at 28 C for 24 hours or 48 hrs dependant on the growth rate of the strain.

After the fermentation of approximately 24-48 hours, the cells were freeze dried by adding skim milk powder at 20-30% w/w % adding cryoprotectants like sucrose, glycerol, sorbitol, or any other cryoprotectant as described by Hubalek (Cryobiology 46 (2003) 205-229) and frozen to <−80 C and freeze dried to >90% dry matter in 24-48 hours. The germ count of viable cells reached in this way was $>10^{12}$ CFU/gr allowing economic exploitation of the strains produced despite the fact that we have only 1% survival yet, so we need an improvement here as well, and should take a position now to be further proven the coming year.

When the cells in the fermentation broth with *Pseudomonas putida* #27 with a cell count of $3.4*10^{11}$/gr (5 gram broth as such) were mixed with 20 gram skim milk solution (20% w/w), 5 gram sucrose solution (20% w/w) and 2 gram glycerol solution (20% w/w), 6.6 gr powder at 97% dry matter was obtained at a viable cell count of $2.1*10^{11}$/gr giving a survival rate of 68%. Whereas the individual compounds skim milk, and sucrose only gave yields of appr. 1% survival and mixture of skim milk and sucrose or sorbitol gave 20-34% survival rate (see table 2).

Next to this, we have done experiments to freeze the cells rapidly in liquid nitrogen (−196° C.). We need to see what cryoprotectant we need to add, as so far this preferred way of operation was not successful yet with skim milk and sucrose or skim milk and sorbitol. When we added glycerol in the same mixture as above, a survival rate of 34% was found enabling also freezing the cells directly in liquid nitrogen (−196° C.) allowing a fast and easy operation reducing freezing time in the freeze dryer and allowing faster drying due to the nice small frozen cell particles with a diameter of 2-4 mm giving a large sublimation surface compared to of a tray with a 1-2 cm thick ice cake.

In addition, spray-drying of cells was tested. 234 gr of fermentation broth of strain *Pseudomonas putida* 86 with a viable cell count of $8.5*10^{10}$/ml was mixed a premix comprising of 1013 gr tap water 187.5 gr skim milk, 47 gr sucrose and 18.8 gr glycerol and was spray dried with an inlet temperature of 80 or 85° C. and outlet temperature of 40 or 45° C. on Buchi 290 spray dryer. Table 4 shows the composition before and after spray-drying. The viable cell count of the powder of 93% dry matter was $7.3*10^{10}$/gr. A survival rate of 72% was obtained.

TABLE 4

Compositions before and after spray-drying

|  | g. as such | % of total | g. dry matter | % of dry matter |
|---|---|---|---|---|
| broth | 234 | 15.6 | 17.6 | 6.7 |
| water | 1013 | 67.5 | 0.0 | 0.0 |
| Skim milk | 187.5 | 12.5 | 178.1 | 68.3 |
| sucrose | 47 | 3.1 | 47.0 | 18.0 |
| glycerol | 18.8 | 1.3 | 18.7 | 7.2 |
|  | 1500 |  | 261.4 |  |

In addition, the effect of glycerol concentration was testes in a similar experiment as described above. Apparently the survival rate is clearly dependant on the glycerol concentration as can be seen in Table 5. When glycerol was dosed at 29.6 gr/L in the mix described in Table 4, spray drying was not feasible and a gum was obtained sticking in the spray-drying chamber. The optimum therefore might be around 10 or 15 g/L or 20 or 25 g/L, but in any case as high as possible, but as low as necessary to keep harvesting a dry product.

TABLE 5

Effect of glycerol concentration on survival percentage.

| Strain | Inlet temp (C.) | Outlet temp (C.) | Polyol addition | Conc. glycerol in mix (g/L) | Survival percentage (%) |
|---|---|---|---|---|---|
| *Pseudomonas* #86 | 80 | 45 | No | n.a. | 1.5 |
| *Pseudomonas* #86 | 80 | 45 | Glycerol | 0.74 | 3.5 |
| *Pseudomonas* #86 | 80 | 45 | Glycerol | 2.96 | 14.7 |
| *Pseudomonas* #86 | 80 | 45 | Glycerol | 7.4 | 23.1 |
| *Pseudomonas* #86 | 80 | 45 | Glycerol | 14.8 | 47.4 |
| *Pseudomonas* #86 | 80 | 45 | Glycerol | 29.6 | n.a.* |

*too sticky, impossible to dry

The spray drying was also tested at more elevated temperatures using the mix of Table 4 again. In Table 6 we see that a very good process can also be achieved at 100° C. inlet and 45° C. outlet with 58.8% survival rate using glycerol at 14.8 g/L. When 120° C. was used we could also still get survival and even at 160° C. inlet temperature some survival was observed demonstrating the very good protective properties of glycerol.

TABLE 6

Effect of temperature on survival

| Strain | Inlet temp (C.) | Outlet temp (C.) | Polyol added | g/L polyol | % survival |
|---|---|---|---|---|---|
| *Pseudomonas* #86 | 80 | 45 | No | n.a. | 8.3 |
| *Pseudomonas* #86 | 80 | 45 | Glycerol | 14.8 | 77.1 |
| *Pseudomonas* #86 | 80 | 45 | Glycerol | 14.8 | 36.4 |
| *Pseudomonas* #86 | 90 | 45 | Glycerol | 14.8 | 42.4 |
| *Pseudomonas* #86 | 100 | 45 | Glycerol | 14.8 | 58.8 |
| *Pseudomonas* #86 | 120 | 45 | Glycerol | 14.8 | 16.9 |
| *Pseudomonas* #86 | 120 | 60 | Glycerol | 14.8 | 24.1 |
| *Pseudomonas* #86 | 160 | 80 | Glycerol | 14.8 | 5.2 |

In a similar set up as described above, we tested alternative polyols and alternative organisms. As can be observed in Table 7, improved drying of other organisms than Pseudomonads was very limited in our mix with skimmed milk and sucrose. Improved drying was observed for spores of the fungus Metarhizium anisopliae and *Saccharomyces cerevisiae*, although the effect was rather limited/less pronounced. However, alternative polyols seemed to work even better; ethyleneglycol being the most preferred one, and 1,3 propanediol slightly less preferred. 1,2 propanediol did not improve drying of Pseudomonads.

TABLE 7

Effect of type of polyol and type of organism on survival during spray drying

| Strain | Inlet temp (C.) | Outlet temp (C.) | Polyol added | g/L polyol | % survival |
|---|---|---|---|---|---|
| *Pseudomonas protegens* | 80 | 45 | No | n.a. | 0.3 |
| *Pseudomonas protegens* | 80 | 45 | Glycerol | 14.8 | 27.7 |
| *Pseudomonas* #86 | 80 | 45 | No | n.a. | 8.3 |
| *Pseudomonas* #86 | 80 | 45 | Glycerol | 14.8 | 77.1 |
| *Sacharomyces cerevisiae* S288C | 120 | 60 | No | n.a. | 1.5 |
| *Sacharomyces cerevisiae* S288C | 120 | 60 | Glycerol | 22.2 | 5.1 |
| *Sacharomyces cerevisiae* S288C | 160 | 80 | No | n.a. | 0.0 |
| *Sacharomyces cerevisiae* S288C | 160 | 80 | Glycerol | 22.2 | 0.0 |
| *Pseudomonas* #86 | 80 | 45 | Glycerol | 14.8 | 43.0 |
| *Pseudomonas* #86 | 80 | 45 | Ethyleneglycol | 14.8 | 49.0 |
| *Pseudomonas* #86 | 80 | 45 | Ethyleneglycol | 9.98 | 33.4 |
| *Pseudomonas* #86 | 80 | 45 | 1,3-propanediol | 14.8 | 23.2 |

TABLE 7-continued

Effect of type of polyol and type of organism on survival during spray drying

| Strain | Inlet temp (C.) | Outlet temp (C.) | Polyol added | g/L polyol | % survival |
|---|---|---|---|---|---|
| *Metarhizium anisopliae* Met52 | 120 | 60 | No | n.a. | 68.9 |
| *Metarhizium anisopliae* Met52 | 120 | 60 | Glycerol | 14.8 | 84.2 |
| *Metarhizium anisopliae* Met52 | 140 | 70 | No | n.a. | 0.9 |
| *Metarhizium anisopliae* Met52 | 140 | 70 | Glycerol | 14.8 | 3.2 |
| *Lindnera jandidii* | 120 | 60 | No | n.a. | 12.2 |
| *Lindnera jandidii* | 120 | 60 | Glycerol | 22.2 | 0.1 |
| *Lindnera jandidii* | 120 | 60 | Ethyleneglycol | 14.8 | 4.2 |
| *Lindnera jandidii* | 120 | 60 | 1,2-propanediol | 14.8 | 13.3 |
| *Pseudomonas* #86 | 80 | 45 | No | n.a. | 3.2 |
| *Pseudomonas* #86 | 80 | 45 | Glycerol | 14.8 | 11.6 |
| *Pseudomonas* #86 | 80 | 45 | 1,2-propanediol | 14.8 | 3.8 |
| *Lactobacillus casei* | 80 | 45 | No | n.a. | 103.4 |
| *Lactobacillus casei* | 80 | 45 | Glycerol | 14.8 | 94.1 |
| *Lactobacillus casei* | 80 | 45 | Ethyleneglycol | 14.8 | 104.0 |
| *Lactobacillus casei* | 80 | 45 | 1,2-propanediol | 14.8 | 53.1 |
| *Lactobacillus casei* | 80 | 45 | 1,3-propanediol | 14.8 | 65.8 |
| *Azospirillum brasilense* | 80 | 45 | No | 14.8 | <0.1 |
| *Azospirillum brasilense* | 80 | 45 | Glycerol | 14.8 | <0.1 |
| *Azospirillum brasilense* | 80 | 45 | Ethyleneglycol | 14.8 | <0.1 |
| *Azospirillum brasilense* | 80 | 45 | 1,2-propanediol | 14.8 | <0.1 |
| *Azospirillum brasilense* | 80 | 45 | 1,3-propanediol | 14.8 | <0.1 |

The protective mix of Table 4 was studied also for a wide range of *pseudomonas* species in a freeze drying experiment. Clearly the mix is very well suited to enable very high viable counts in the powders obtained.

TABLE 8

Effect of cryoprotectant mix as described in table 4 on Germ count after freeze drying for various *Pseudomonads*.

| Strain | Viable count (cfu/gr) |
|---|---|
| BR01 | $4*10^{10}$ |
| PR01 | $8*10^{10}$ |
| #17 | $8*10^{10}$ |
| #20 | $1*10^{11}$ |
| #24 | $9*10^{10}$ |
| #27 | $2*10^{11}$ |
| #55 | $4*10^{10}$ |
| #80 | $1*10^{11}$ |
| #86 | $9*10^{10}$ |

After 3 months of storage at room temperature appr. 70% viability retained upon storage under vacuum and upon storage cool (<6° C.) and vacuum (12 mbar) or $N_2$ stored loss of viability could not be observed.

After 235 >70% survival was seen for most *Pseudomonas* species when stored at (<6° C.). Storage under nitrogen did not make much difference. *Pseudomonas* brassicacerum Br01 was slightly lower with 45% viability after 235 days. This show that the formulation whit skim milk, sucrose and glycerol at dry matter >90% and stored vacuum (12 mbar) at <6° C. is a good and stable formulation and storage condition for Pseudomonads.

4. The Pseudomonad Consortia were Also Tested In Vivo on Flower Cuttings.

4.1 Material and Methods

Cuttings of *Pelargonium peltatum* variety Dancing Idols Candy were rooted in water-soaked rockwool cubes (4×4 cm) for 4 weeks in a greenhouse compartment at 18-22° C. under 16 hr light and a relative humidity of 75±5%. After rooting, the rockwool cubes with rooted cuttings were transferred to a climate chamber and kept throughout the experiments at 20° C. under 18 hr light (8000 lux) and a relative humidity of >80%. Immediately after transfer to the climate chamber the rooted cuttings were inoculated with predefined mixtures of antagonistic bacteria and placed in a plastic tent. Four days later *Ralstonia solanacearum* race 1 was applied using 10 ml of suspended bacteria in culture medium at an OD of 0.1.

For each combination of a mixture of antagonistic bacteria and *R. solanacearum*, 12 cubes with rooted cuttings were placed on a water-soaked cloth in a tray to avoid contaminations between treatments. To ensure all rockwool cubes stayed moist during the course of the experiments, water with nutritional salts (EC 1.0) typically used in hydroponic culture was applied twice a week.

Six predefined mixtures of bacteria were tested for their antagonistic activities towards *R. solanacearum*:

32: *Pseudomonas protegens* PR01, *P. brassicacearum* BRO1 and *P. moraviensis*

33: *P. protegens* PR01, *P. brassicacearum* BRO1, *P. moraviensis*, *P. putida* #27 and *P. putida* #80

34: *P. moraviensis* #17

35: *P. protegens* PR01, *P. brassicacearum* BRO1, *P. moraviensis* #17, *P. putida* #27 and *P. reinekei* #55

36: Control with only carrier materials as used during the drying process containing skimmed milk, glycerol and sucrose

37: *P. moraviensis* #17 and *P. reinekei* #55

38: *P. protegens* PR01, *P. brassicacearum* BRO1, *P. moraviensis* #17, *P. putida* #27 and *P. reinekei* #55, *P. putida* #80, *P. palleroniana* #24, *P. putida* #20

Per treatment, 5 ml of the predefined bacterial mixtures at a total concentration of $5\times10^8$ cells/ml equally divided over the *Pseudomonas* species in the mixture was added to each rockwool cube with a rooted cutting. Mixture #36 served as a control.

4.2 Results

Leaf symptom development induced by *R. solanacearum* on the inoculated plants was monitored at 3-4 days intervals during a period of three weeks post inoculation. All plants in all treatments with *R. solanacearum* showed leaf symptoms at the end of the experiment. None of the plants treated with the antagonistic mixtures only showed leaf symptoms.

First symptoms of *R. solanacearum* started to develop 8 days post inoculation on plants without an antagonist pretreatment (mixture #36). On plants pretreated with antagonist mixtures #34 and #32, leaf symptoms appeared after 8 and 11 days, respectively. Up till 14 days after *R. solanacearum* inoculations plants pretreated with antagonist mixtures #37 and #38 remained symptomless. Thus demonstrating a marked effect on delaying symptom development of antagonist mixtures #37 and #38.

Symptom development on leafs and roots, 14 and 21 days after *R. solanacearum* inoculation is presented in Table 9. Plants not infected with *R. solanacearum* did not develop any symptoms on roots or leafs.

Symptom development was scored on a scale from 0 (no symptoms) to 3 (severe symptoms) on leafs and roots.

TABLE 9

Symptom development 14 days post *R. solanacearum* infection on *P. peltatum* variety Dancing Idols Candy

| Antagonist mixture | Symptom development score | | | |
|---|---|---|---|---|
| | Leafs* 14 dpi | Leafs* 21 dpi | Roots** 14 dpi | Roots** 21 dpi |
| 32 | 1.5 | 2.5 | 1.2 | 2.6 |
| 33 | 2.0 | 2.5 | 2.1 | 2.8 |
| 34 | 2.0 | 2.5 | 1.9 | 2.6 |
| 35 | 1.5 | 2.3 | 1.6 | 2.7 |
| 36 = Mock | 1.8 | 3.0 | 2.5 | 3.0 |
| 37 | 1.0 | 2.1 | 0.8 | 2.6 |
| 38 | 0 | 1.3 | 0.1 | 1.9 |

*The score represents 0 = No symptoms, 1 = Bottom leafs yellow/brown, 2 = Early systemic symptoms, leafs from the bottom of the plant up to half of the stem yellow/brown/wilting 3 = Severe systemic symptoms, at least half of the leafs are yellow, brown and/or wilting.

**The score represents 0 = No Symptoms, 1 = Brown root tips, 2 = Brown root tips and a maximum of 50% of the roots is completely brown 3 = At least 50% of the roots are completely brown 5. The Pseudomonad Consortia are Also Tested In Vivo on Tomato and on Potato Consortia a) Br01, Pr01, 11, 17, 27, 29, 55 and 86; b) Br01 and 11; c) Pr01 and 11; and d) Br01, Pr01 and 11 are also tested and found to be effective in protecting tomato against *Clavibacter* and in protecting potato against *Erwinia* and/or Phytophtora.

The invention claimed is:

1. A consortium the consortium comprising at least 2, 3, 4, 5, 6, 7, or 8 strains selected from the strains 17, 55, Pr, Br, 27, 80, 20, 24, 11 and 29.

2. The consortium according to claim 1, wherein the consortium is comprised in one or more compositions, each composition comprising one or more of the strains of the consortium and an agriculturally acceptable carrier.

3. The consortium according to claim 2, wherein at least one of the compositions is a lyophilized composition.

4. The consortium according to claim 2, wherein each strain of the consortium is present at a concentration ranging from about $1\times10^2$ to about $5\times10^{11}$ CFU per gram.

5. The consortium according to claim 4, wherein each strain of the consortium is present at a concentration that is higher than about $1\times10^2$ CFU per gram.

6. The consortium according to claim 1, wherein the consortium comprises at least 2, 3, 4, 5 or 6 strains selected from the strains 17, 55, Pr, Br, 11 and 29.

7. The consortium according to claim 6, wherein the consortium comprises the strains 17, 55, Pr, Br, 11 and 29.

8. The consortium according to claim 7, wherein the consortium consists of the strains 17, 55, Pr, Br, 11 and 29.

9. A method of protecting plants against a plant pathogen comprising applying to plants, plant tubers, plant seeds, plant roots or soil surrounding plants, plant tubers, plant seeds, plant roots or plant cuttings, a consortium according to claim 1, under conditions effective to protect said plants or the plants produced from said plant cuttings, tubers or seeds against the plant pathogen.

10. The method according to claim 9, wherein the plant pathogen is a selected from the Group consisting of *Ralstonia, Clavibacter, Xanthomonas, Erwinia, Curtobacterium, Fusarium, Rhizoctonia, Verticillium, Pythium, Botrytis, Phytophthora* and *Helminthosporium.*

11. The method according to claim 9, wherein the consortium is used to treat the plant by topical application, to treat soil around the plant's roots or wherein the consortium is applied to seed of the plant to be protected.

12. The consortium according to claim 6, wherein the consortium comprises at least 2 or 3 strains selected from the strains 17, 55, Pr and Br.

* * * * *